United States Patent [19]

Ghaderi

[11] Patent Number: 4,594,506
[45] Date of Patent: Jun. 10, 1986

[54] GAS CHROMATOGRAPH/MASS SPECTROMETER INTERFACE

[75] Inventor: Sahba Ghaderi, Madison, Wis.

[73] Assignee: Nicolet Instrument Corporation, Madison, Wis.

[21] Appl. No.: 648,518

[22] Filed: Sep. 10, 1984

[51] Int. Cl.⁴ ............................................. H01J 47/04
[52] U.S. Cl. .................................... 250/288; 250/282
[58] Field of Search ............ 250/288, 282, 281, 423 R

[56] References Cited

U.S. PATENT DOCUMENTS 4,296,322 10/1981 Wechsung ........................... 250/282

FOREIGN PATENT DOCUMENTS 0083472 7/1983 European Pat. Off. ............ 250/288

OTHER PUBLICATIONS

Smith et al., Analytical Chemistry, vol. 53, No. 11, Sep. 1981, pp. 1603-1611.

*Primary Examiner*—Bruce C. Anderson
*Assistant Examiner*—Jack I. Berman
*Attorney, Agent, or Firm*—Kinney & Lange

[57] ABSTRACT

A gas chromatograph/mass spectrometer interface for obtaining a mass spectrometer sample from the effluent of a gas chromatograph. The sample obtained in accordance with the present invention is essentially devoid of any carrier gas. A recording medium is located within a housing into which the effluent from the gas chromatograph is introduced. The temperature of the recording medium is below the freezing point of the sample portion of the effluent, such that the sample portion will freeze on the recording medium. A pressure regulator maintains a positive pressure within the housing to facilitate removal of the carrier gas portion of the effluent. The recording medium is transported within the housing during the freezing process such that different components of the sample are deposited on different portions of the recording medium. The sample is released from the recording medium for introduction into the mass spectrometer by heating the recording medium.

23 Claims, 2 Drawing Figures

GAS CHROMATOGRAPH/MASS SPECTROMETER INTERFACE

BACKGROUND OF THE INVENTION

1. Field of the Invention

The present invention relates to the preparation of a mass spectrometer sample from the effluent of a gas chromatograph.

2. Description of the Prior Art

Gas chromatography is very useful as a separator of compounds, while a mass spectrometer is an excellent instrument for identifications. An effective interface would allow each instrument to operate in sequence, without degrading the performance of either. By separating the components of a specimen in a gas chromatograph, more accurate determinations with a mass spectrometer appear possible. However, interfacing a gas chromatograph with a mass spectrometer presents two problems: (1) separation of the sample from the chromatograph carrier gas; and (2) the time between the different chromatograph peaks as they reach the mass spectrometer as compared to the necessary or desired scanning time of the spectrometer.

The first problem noted above arises from the fact that gas chromatographs normally operate at pressures greater than 760 torr, while mass spectrometers function best at high vacuums in the $10^{-5}$ torr range, or greater. Fourier Transform mass spectrometers operate optimally near $10^{-8}$ torr. Thus, an interface between a gas chromatograph and a mass spectrometer has required a "throwing away" of some or most of the sample, with the resultant loss of sample size sensitivity. This problem is even more pronounced with packed column gas chromatographs due to the higher quantity of carrier gas in the column which must be removed before the sample can be introduced into the mass spectrometer.

The customary approach for overcoming the problems due to the pressure differences between the two instruments is to separate the carrier gas from the sample. Conventional methods of separating the carrier gas include: effluent splitting or Watson Biemann separators; jet separators; and molecular separating membranes. These methods provide differing degrees of sample enrichment, but none provide 100% sample transmission.

Watson Biemann separators are based on the concept of enrichment by diffusion. The lighter carrier gas molecules permeate an effusion barrier, such as sintered glass, in preference to the heavier organic sample molecules and can be removed by a vacuum system. Although the separation procedure does increase the sample-to-carrier gas ratio approximately 50 times, less than 50% of the sample passes into the mass spectrometer, resulting in a decrease in sensitivity due to the smaller sample size.

A precisely aligned, supersonic jet/orifice system may also be used to remove the carrier gas using the effusion principle. As the gas chromatograph effluent passes through a small jet, the stream is directed toward an orifice. The concentration of carrier gas increases away from the center line while the concentration of the sample tends to increase toward the center. The orifice intercepts only the center portion of the stream. Two such jet/orifice assemblies may be used in series if desired. Using this method, approximately 60% of the sample is transmitted to the mass spectrometer with a sample enrichment of approximately 100.

Molecular membrane separators take advantage of differences in the permeability rate of the sample and the carrier gas through a silicone rubber membrane. The column effluent from the gas chromatograph passes a thin rubber membrane. The carrier gas usually has a low permeability and is not adsorbed by the membrane, whereas the organic molecules are adsorbed and pass through the membrane and directly into the high vacuum of the mass spectrometer. Sample transmission rates vary between 50 and 90 percent, and the enrichment factor is approximately 1000.

Another technique is disclosed in U.S. Pat. No. 3,896,661 to Parkhurst et al which proposes the use of thin layer chromatography of the mixture to be analyzed. The organic portion of the effluent of a gas chromatograph is placed on a chromatographic medium. The sample components migrate at different rates on the medium. The medium is then selectively heated to sublime the adsorbed chemical substance directly into the ion source of the mass spectrometer. U.S. Pat. No. 4,267,457 to Nakagawa et al shows a similar system in which a sample holding element is composed of a porous and gas permeable aggregate of ingredients which allow the components of a sample to separate to form a chromatogram.

The systems of the above noted patents do not use a gas chromatograph and thus do not deal with the interface between a gas chromatograph and a mass spectrometer. Indeed, the separation of the sample components does not utilize the precise separation capabilities of a gas chromatograph in connection with a mass spectrometer to enhance the analysis of the sample.

The second noted problem which arises when interfacing gas chromatographs to mass spectrometers is the small time interval that may exist between two or more components in the gas chromatograph effluent. If the time required for scanning over the mass range of interest is longer than the time between the chromatograph peaks, the resulting mass spectrum is a mixture of the components. In the case of high resolution, capillary column gas chromatographs, the time between peaks can be less than a second. This has limited the gas chromatograph/mass spectrometer performance for all types of mass spectrometers and made it impossible to take full advantage of the capabilities of the high resolution mass spectrometers when interfaced with a gas chromatograph.

Although the Fourier transform mass spectrometer is a fast scanning instrument (up to 100 scans/second), the use of this speed in capillary gas chromatograph interfacing is not practical for several reasons. First, mass resolution obtained under such fast scanning rates is poor. Second, the signal-to-noise ratio is low due to the lack of time for adequate signal averaging of each gas chromatograph peak. To achieve high resolution mass spectra, detection time in the order of one second is needed. For a good signal-to-noise ratio, signal averaging for a few seconds is desirable. A third, but less important, problem with this method is the lack of time for Fourier transformation and the necessity of a large storage module in which to "dump" all of the raw data for later transformation.

SUMMARY OF THE INVENTION

The present invention is directed to obtaining a mass spectrometer sample from the effluent of a gas chromatograph. The sample obtained is essentially devoid of any carrier gas. The present invention includes a recording medium located within a housing on which the sample portion of the effluent is frozen. The apparatus also includes a means for introducing the effluent from the gas chromatograph into the housing, a cooling means for lowering the temperature of the recording medium below the freezing point of the sample portion of the effluent and a pressure regulator for maintaining a positive pressure within the housing to facilitate removal of the carrier gas portion of the effluent. The recording medium is transported within the housing during the freezing process so that the different components of the sample are deposited upon different portions of the recording medium. In this way, the carrier gas is removed from the system so that the mass spectrometer can operate at a high vacuum.

To introduce the resultant, recorded sample into the mass spectrometer, the recording medium is first returned to its original position within the housing. The medium is once again moved, and a heater heats the recording medium so that the sample portion is evaporated from the recording medium. The sample is then pumped into the mass spectrometer. The recording medium may be moved at a rate dependent on the scanning time of the mass spectrometer which makes the sample introduction rate independent of the time interval between the peaks or components in the gas chromatograph effluent.

DETAILED DESCRIPTION OF THE PREFERRED EMBODIMENT

Figure 1:
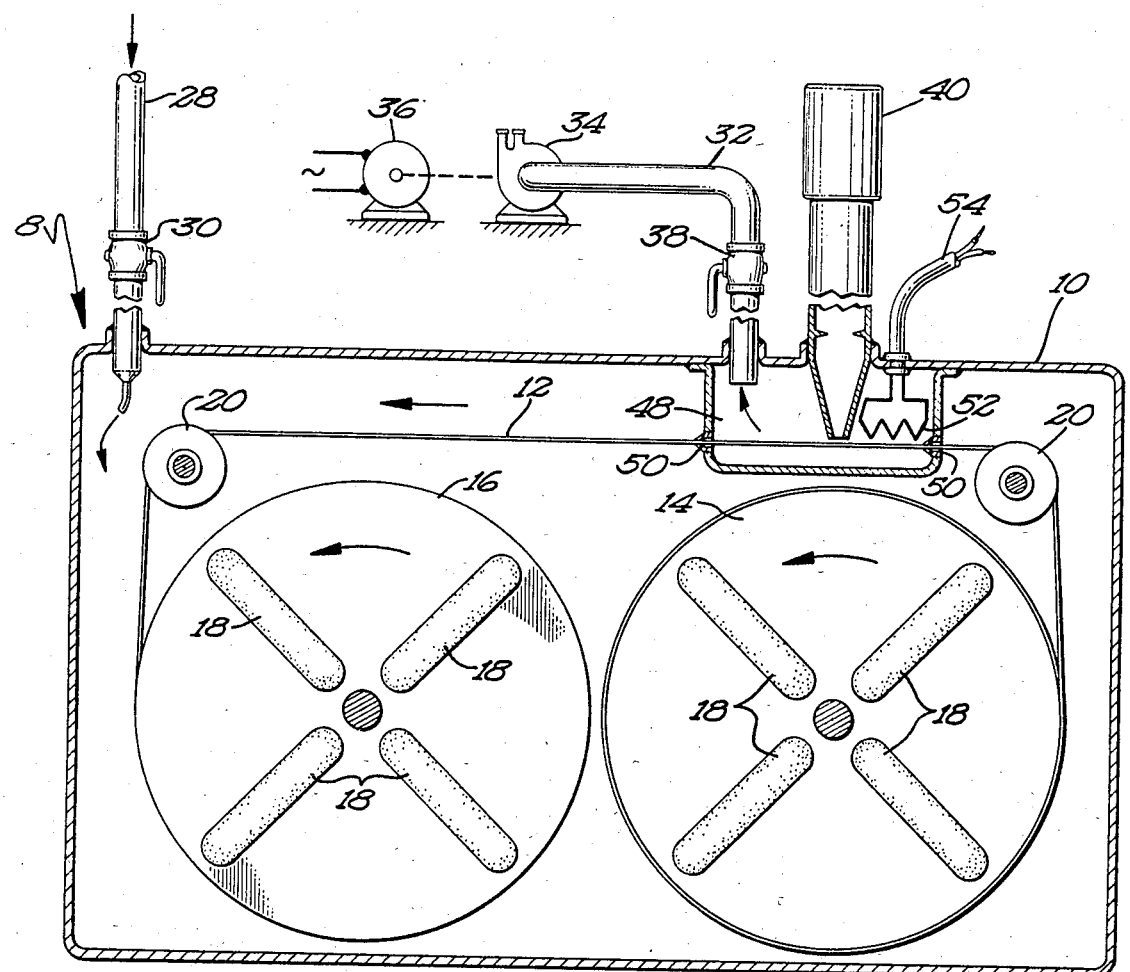
FIG. 1 shows a cut-away view of a portion of the present invention.
Figure 2:
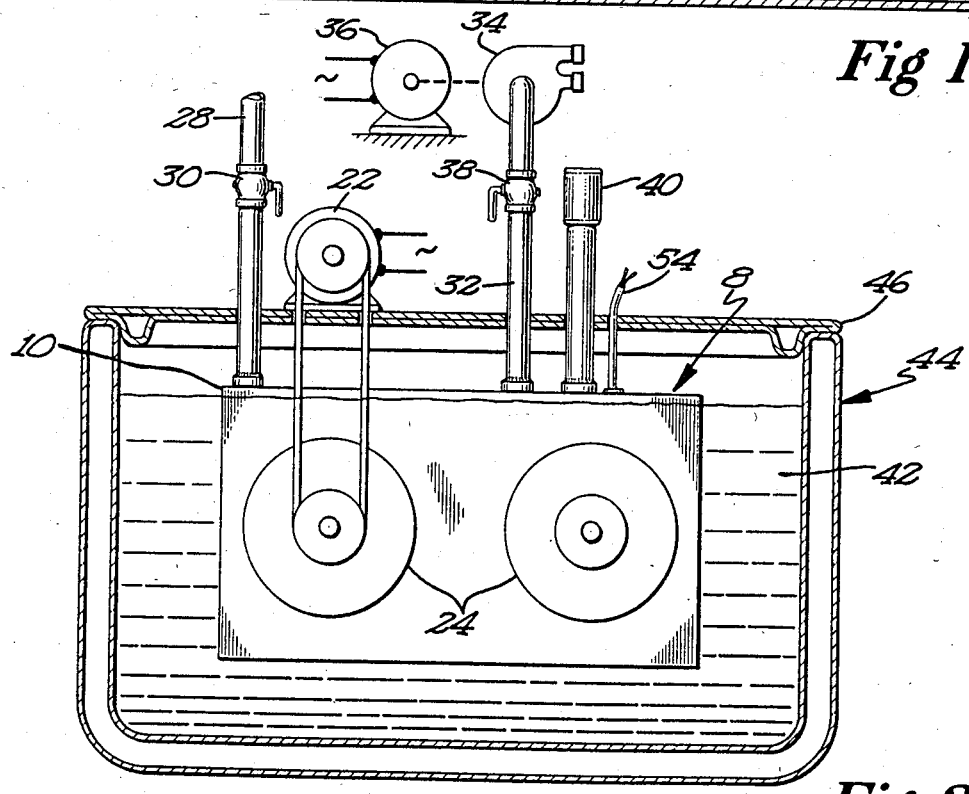
FIG. 2 shows a preferred embodiment of the present invention incorporating the portion illustrated in FIG. 1.

FIG. 1 and FIG. 2 show gas chromatograph/mass spectrometer interface cassette designated generally at 8. A housing 10 is constructed of a non-magnetic material, such as stainless steel. A metal tape 12, such as stainless steel, is wound on and between a supply reel 14 and a takeup reel 16. The diameters of reels 14 and 16 are relatively large as compared to the thickness of the tape to lessen the effect of the change of radius as the tape 12 is wrapped or unwrapped over the reels and itself. The reels 14 and 16 are constructed of aluminum or other non-magnetic material and carry iron bars 18, for reason to be described below. Non-magnetic tape guide rollers 20 direct the movement of the tape within the housing.

Movement of the metal tape 12 between supply reel 14 and takeup reel 16 is controlled by an external motor 22 (see FIG. 2). The motor 22 drives a magnet wheel 24 through an appropriate drive mechanism, such as belt 26 and associated pulleys. The magnet wheel 24 is positioned outside of the housing 10 and is magnetically coupled to the bars 18 of either the supply reel 14 or takeup reel 16. The motor 22 can be a stepper motor under computer control for preprogrammed movement. Rotation of the magnet wheel will result in rotation of the associated reel and movement of the metal tape 12. A separate motor and drive may be provided for each magnet wheel 24.

Three gas connections are made with the interior of the housing 10. Purge gases, such as nitrogen or helium, are introduced into the housing 10 via purge gas port 28. The flow rate is controlled by valve 30. The pressure in the housing is lowered into the high vacuum range by evacuating housing 10 through vacuum port 32 using pump 34, which is operated by pump motor 36 and control valve 38. In addition, a high vacuum connector 40 is provided which is alternatively connected to either the gas chromatograph (not shown) or the mass spectrometer (not shown).

Care must be taken in the construction of the interface cassette 8 to ensure high vacuum performance. The cassette 8 can be made of 316 stainless steel or aluminum. No magnetic material should be used so as to avoid interference with the magnetic drive mechanism. However, other drives may permit the use of mgnetic materials. Magnetic coupling is preferred in that it does not require a physical penetration of the cassette. The housing 10 and all joints and valves should be leak-proof and helium-tested to be certain that it can provide a vacuum of $10^{-10}$ torr or better. To avoid contamination, no lubricating materials with vapor pressure greater than $10^{-7}$ torr at room temperature should be used within the housing 10.

Before recording the gas chromatograph effluent, the metal tape 12 should be pre-cooled. This can be done conveniently by immersing the interface cassette 8 in liquid nitrogen 42 that is contained in a Dewar flask 44 having a suitable cover 46 (see FIG. 2). This environment will also allow the interface cassette 8 to be kept cold during recording and after. To avoid water condensation on the cold metal tape and on the walls of the cassette, it is recommended that the cassette be purged with dry cold nitrogen or helium during cooling. This can be done using the purge gas port 28 as a purge gas entrance and the high vacuum connector 40 as an exit. Vacuum port 32 is closed via the control valve 38 during the cool-down period.

During recording of the gas chromatograph effluent on the cold metal tape 12, the control valve 38 is open and purge gas is pumped out of cassette 8 through vacuum port 32 by operation of the pump 34. The outlet of the gas chromatograph column is then interconnected with the cassette 8 via high vacuum connector 40. This interconnection can be either a direct connection to the connector 40 or by a proper transfer line. A slow gas purge through purge port 28 during the recording ensures a positive pressure within the housing 10 and prevents possible contamination of the rest of the metal tape 10. That is, the positive pressure established through port 28 and the removal of gas through port 32, whose inlet is adjacent the connector 40, prevent or reduce the migration throughout the housing of effluent entering through the connector 40. Additionally, the possibility of contamination may be further reduced by isolating the gas chromatograph effluent sample from the rest of the metal tape by use of a sample cell 48. The cell 48 has inlet and outlet apertures 50 which allow the metal tape 12 to move through the cell 48.

During recording, it may be desirable to keep the sample cell 48 warm or at room temperature to avoid condensation of the effluent sample on the walls of the cell 48 instead of the metal tape 12. If that is the case, a small heater 52 can be installed within the cell 48 and connected to appropriate electrical conductors 54.

After injection of the sample into the gas chromatograph, recording is started. The speed of the metal tape 12 during recording should be chosen based on the resolution and widths of the gas chromatograph peaks.

Movement of the tape 12 is controlled by motor 22. During recording, organic compounds will freeze on the metal tape 12. The carrier gas has a much lower freezing point and does not freeze on the tape 12 and is pumped out through vacuum port 32. The recording continues until the sample has completely passed through the gas chromatograph. For example, if metal tape with a thickness of 0.001 inch wrapped on a 7 cm diameter reel, a wrapped thickness of 0.5 cm (a total diameter of reel and tape of 7.5 cm) will last for approximately 37 minutes of recording at a tape speed of 2 cm/second.

After the recording is completed, the metal tape 12 may be stored for an indefinite length of time as long as the interface cassette 8 is kept cold, such as in liquid nitrogen. During storage, purge gas valve 30 and control valve 38 should be closed and the high vacuum connector 40 should be blanked off.

In order to transfer the recorded sample to a mass spectrometer, the interface cassette must be connected to the mass spectrometer via the high vacuum connector 40. The housing 10 must first be pumped out using a roughing pump. Either port 28 or port 32 may be employed. After the internal pressure of the housing 10 reaches milli-torr range, it is pumped to ultra high vacuum. With valves 30 and 38 closed and the cassette 8 under high vacuum and cold, the metal tape 12 must be rolled back to supply reel 14. This can be done by connecting motor 22 to the magnetic wheel 24 associated with the supply reel 14 and rewinding the tape 12. If desired, two motors can be used in order to move the tape in both the forward and rewind directions.

The frozen sample on tape 12 can now be transferred to the mass spectrometer by moving the tape 12 at the proper speed and heating the tape 12 locally by use of heater 52. The heating causes the organic materials to evaporate off of the tape to be pumped into the mass spectrometer, through the high vacuum connector 40, for analysis. Sample pressure in the mass spectrometer source can be adjusted by controlling the current through the heater 52 and/or the speed of the tape. In addition, an adjustable time separation for analysis of different compounds can be obtained by controlling the movement of the tape.

Obviously, many modifications and variations of the present invention are possible in light of the above teachings. For example, it may be desirable to put grooves on the tape 12 or to coat the back of the metal tape 12 with some non-volatile, non-stick material to prevent the transfer of frozen sample from one layer of wrapped tape 12 to the layer above. Also, the heating of the tape 12 to evaporate the sample can be done using a laser source. This allows multiple mass analyses of a single gas chromatograph run by only partially evaporating the sample and storing the rest. It should also be noted that the present invention also allows mass analysis of a single gas chromatograph run under different mass spectrometry conditions. This is possible by merely stopping the tape and changing the mass spectrometer parameters during or between each gas chromatograph peak. It is therefore to be understood that the present invention may be practiced otherwise than as specifically described.

I claim:

1. Apparatus for obtaining a mass spectrometer sample from the effluent of a gas chromatograph, the sample being essentially devoid of any chromatograph carrier gas, the apparatus comprising:

recording means located within a housing;

means introducing the gas chromatograph effluent into the housing;

cooling means lowering the temperature of the recording means for freezing the non-carrier gas portion of the effluent on the surface of the recording medium; and means for removing the carrier gas portion of the effluent from the housing.

2. The apparatus of claim 1 wherein the housing is non-magnetic.

3. The apparatus of claim 1 wherein the recording means comprises a metal strip.

4. The apparatus of claim 1 wherein the recording means comprises a metal tape.

5. The apparatus of claim 4 wherein the metal tape is comprised of stainless steel.

6. The apparatus of claim 1, further comprising tape transport means.

7. The apparatus of claim 6 wherein the tape transport means comprises:

tape supply and take-up roller means located within the housing, the roller means being non-magnetic; and magnetic drive means for rotating the rollers.

8. The apparatus of claim 7 wherein the magnetic drive means comprises:

magnetic means affixed to the tape supply and take-up roller means; and magnet means attached to motor means outside the housing for rotating the roller means without penetration of the housing.

9. The apparatus of claim 8 wherein the motor means is a variable speed stepper motor.

10. The apparatus of claim 1, further comprising means isolating a portion of the recording means from the remainder of the recording means within the housing.

11. The apparatus of claim 10 wherein the isolating means comprises:

sample cell means for receiving the effluent from the gas chromatograph; and entrance and exit aperture means in the sample cell for passing a portion of the recording means through the sample cell.

12. The apparatus of claim 11 further comprising:

vacuum means interfaced with the sample cell for lowering the pressure within the sample cell.

13. The apparatus of claim 12 wherein the vacuum means comprises a pump.

14. The apparatus of claim 11 further comprising:

means for interfacing the sample cell means with a mass spectrometer.

15. The apparatus of claim 1, further comprising heating means.

16. The apparatus of claim 15 wherein the heating means is a filament.

17. The apparatus of claim 15 wherein the heating means is a laser.

18. The apparatus in claim 1 further comprising pressure regulating means for maintaining a positive pressure within the housing which includes purge gas means.

19. The apparatus in claim 18 wherein the purge gas means comprises nitrogen gas.

20. The apparatus in claim 18 wherein the purge gas means comprises helium gas.

21. A method for obtaining a mass spectrometer sample from the effluent of a gas chromatograph, the sample being essentially devoid of any chromatograph carrier gas, the method comprising the steps of:

cooling a metal tape within a housing;

purging moisture from the housing;

connecting the housing to the output of the gas chromatograph;

injecting a specimen into the gas chormatograph;

freezing a portion of the chromatograph effluent on the surface of the metal tape; and removing the carrier gas from the housing.

22. The method of claim 21 further comprising the step of moving the tape at a first predetermined speed.

23. The method of claim 21 wherein the step of moving the tape comprises the step of moving the tape from a supply reel to a take-up reel and the steps of:

rewinding the metal tape from the take-up reel to the supply reel;

connecting the housing to the input of the mass spectrometer;

moving the tape at a second predetermined speed from the supply reel to the take-up reel;

heating a portion of the metal tape so that the sample evaporates from the tape; and delivering the sample into the mass spectrometer.

* * * * *